(12) United States Patent
Aoki et al.

(10) Patent No.: US 10,987,014 B2
(45) Date of Patent: Apr. 27, 2021

(54) INFORMATION PROCESSING APPARATUS, INFORMATION PROCESSING SYSTEM, AND NON-TRANSITORY COMPUTER READABLE MEDIUM

(71) Applicant: Agama-X Co., Ltd., Tokyo (JP)

(72) Inventors: Kosuke Aoki, Tokyo (JP); Mai Suzuki, Tokyo (JP); Kiyoaki Okamoto, Tokyo (JP); Naoki Okamoto, Tokyo (JP); Koji Bito, Tokyo (JP); Takayuki Nakamura, Tokyo (JP); Kenji Akiba, Tokyo (JP); Kengo Tokuchi, Tokyo (JP)

(73) Assignee: AGAMA-X CO., LTD., Tokyo (JP)

( * ) Notice: Subject to any disclaimer, the term of this patent is extended or adjusted under 35 U.S.C. 154(b) by 275 days.

(21) Appl. No.: 16/107,083

(22) Filed: Aug. 21, 2018

(65) Prior Publication Data
US 2019/0231212 A1 Aug. 1, 2019

(30) Foreign Application Priority Data
Jan. 29, 2018 (JP) .............................. JP2018-013022

(51) Int. Cl.
| | | |
|---|---|---|
| *A61B 5/0476* | (2006.01) | |
| *A61B 5/16* | (2006.01) | |
| *A61B 5/00* | (2006.01) | |
| *G16H 10/60* | (2018.01) | |
| *G06F 3/01* | (2006.01) | |
| *G16H 50/20* | (2018.01) | |
| *G16H 40/63* | (2018.01) | |

(52) U.S. Cl.
CPC ............ *A61B 5/0476* (2013.01); *A61B 5/165* (2013.01); *A61B 5/7296* (2013.01); *G06F 3/015* (2013.01); *G16H 10/60* (2018.01); *G16H 40/63* (2018.01); *G16H 50/20* (2018.01); *A61B 2560/0223* (2013.01)

(58) Field of Classification Search
CPC ........ G06F 3/015; G16H 40/63; G16H 50/20; G16H 10/60; A61B 5/165; A61B 5/7296; A61B 5/0476; A61B 2560/0223
See application file for complete search history.

(56) References Cited

U.S. PATENT DOCUMENTS

2015/0351655 A1* 12/2015 Coleman .............. A61B 5/0482 600/301

FOREIGN PATENT DOCUMENTS

JP    H08-215164 A    8/1996

\* cited by examiner

*Primary Examiner* — Christine H Matthews
*Assistant Examiner* — Joshua Daryl D Lannu
(74) *Attorney, Agent, or Firm* — Hoffman Warnick LLC

(57) ABSTRACT

An information processing apparatus includes an acquisition unit, an association unit, and a guide unit. The acquisition unit acquires biological information of a user. The association unit associates the acquired biological information with a specific state of the user. The guide unit guides the user to the specific state. A reference to be used for association with the specific state by the association unit is calibrated by using the biological information, the biological information being acquired from the user who is guided to the specific state by the guide unit.

16 Claims, 10 Drawing Sheets

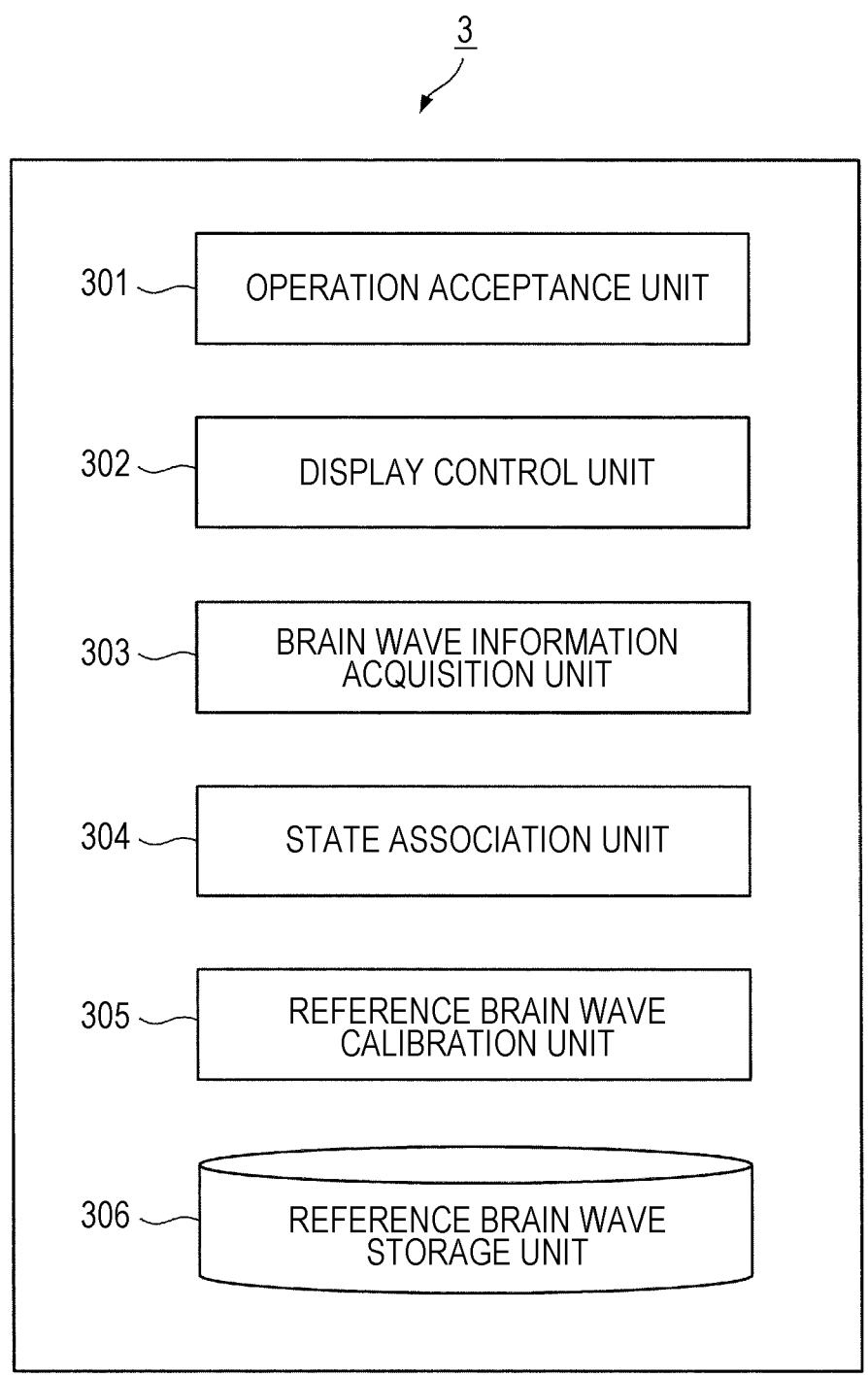

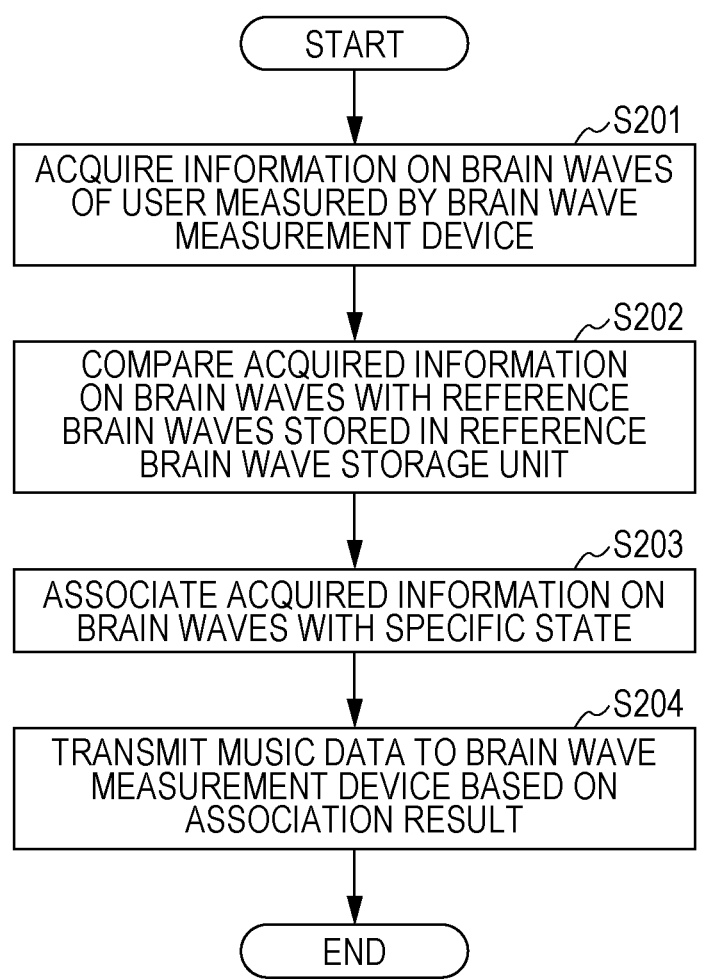

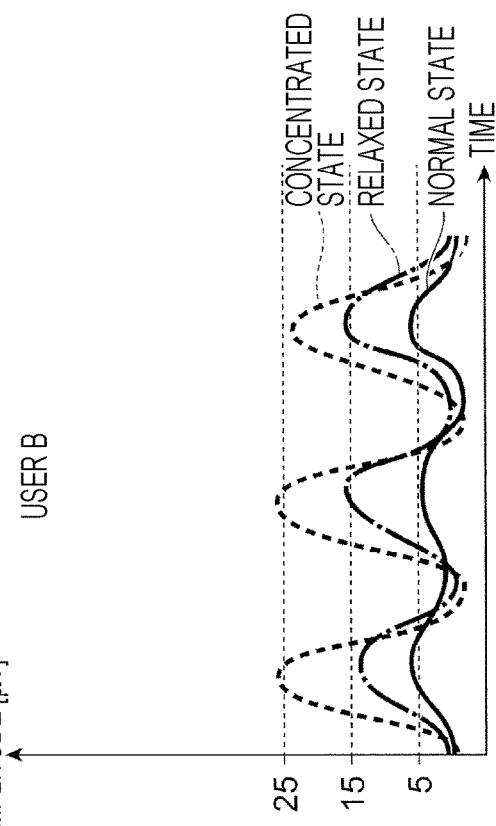
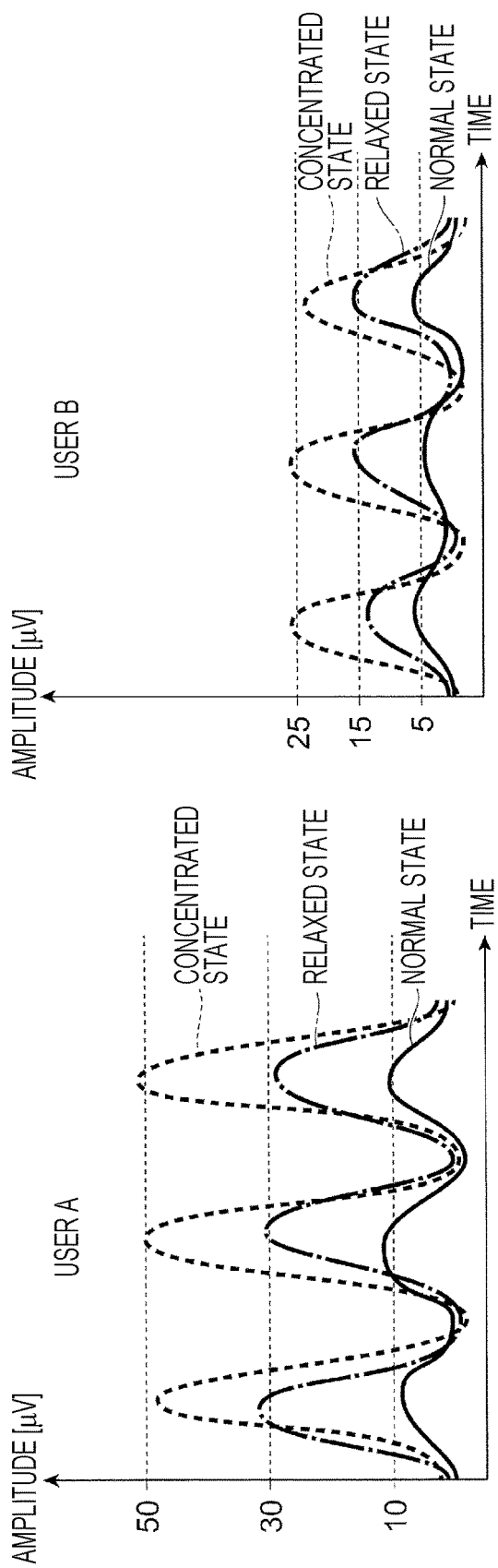
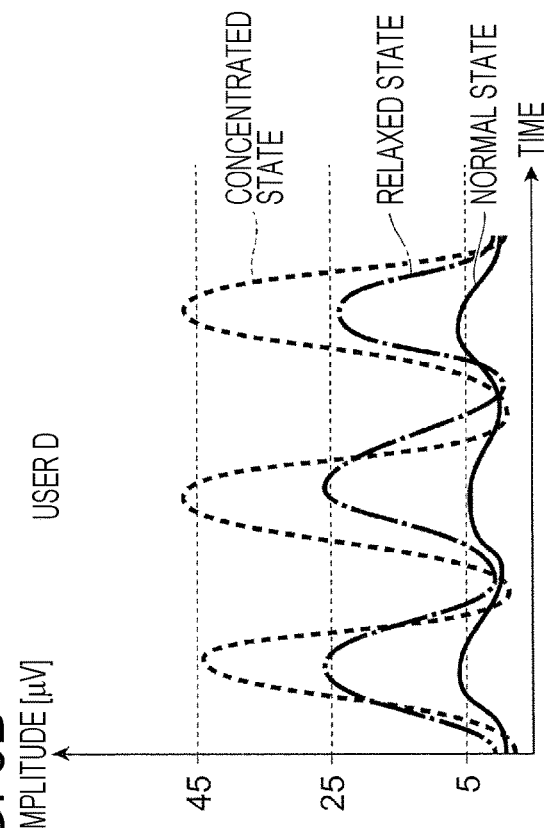
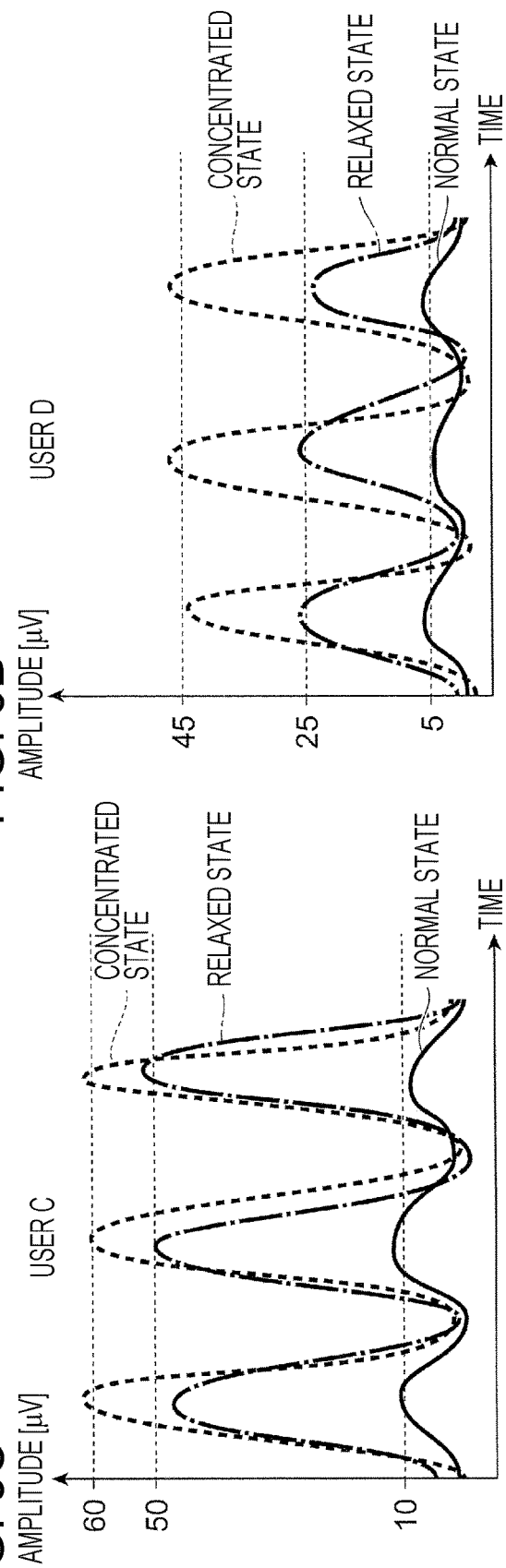

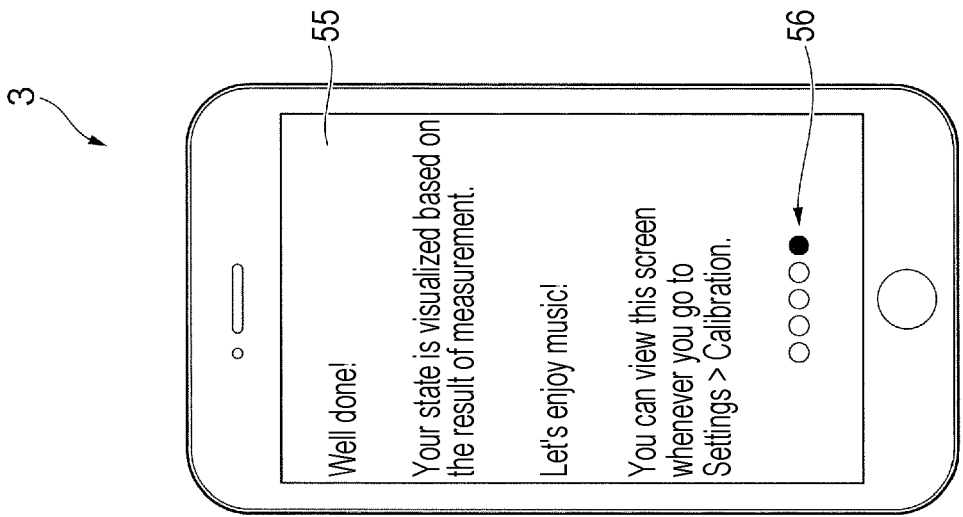
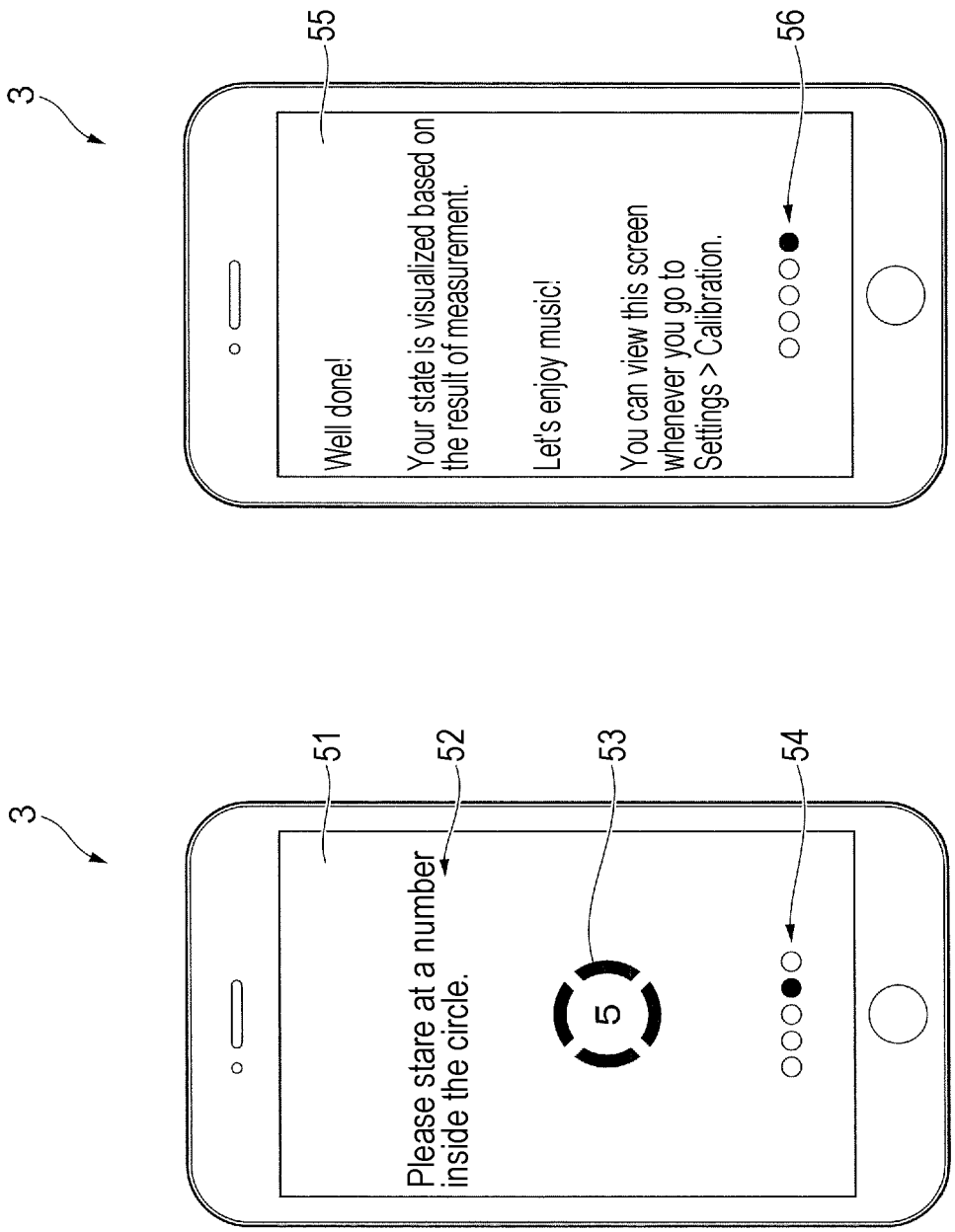

INFORMATION PROCESSING APPARATUS, INFORMATION PROCESSING SYSTEM, AND NON-TRANSITORY COMPUTER READABLE MEDIUM

CROSS-REFERENCE TO RELATED APPLICATIONS

This application is based on and claims priority under 35 USC 119 from Japanese Patent Application No. 2018-013022 filed Jan. 29, 2018.

BACKGROUND

(i) Technical Field

The present disclosure relates to an information processing apparatus, an information processing system, and a non-transitory computer readable medium.

(ii) Related Art

There are techniques for sensing biological information such as brain waves. For example, Japanese Unexamined Patent Application Publication No. 08-215164 discloses a technique for removing noise from a brain wave signal and shaping the waveform of the brain wave signal.

SUMMARY

Since biological information acquired from users differs in individuals, it is necessary that biological information be calibrated for each individual user when the biological information is used. However, it is difficult for a user to calibrate biological information when associating the biological information with a specific state of the user.

Aspects of non-limiting embodiments of the present disclosure relate to a technique that enables a user to calibrate biological information when associating the biological information with a specific state of the user.

Aspects of certain non-limiting embodiments of the present disclosure address the above advantages and/or other advantages not described above. However, aspects of the non-limiting embodiments are not required to address the advantages described above, and aspects of the non-limiting embodiments of the present disclosure may not address advantages described above.

According to an aspect of the present disclosure, there is provided an information processing apparatus including an acquisition unit, an association unit, and a guide unit. The acquisition unit acquires biological information of a user. The association unit associates the acquired biological information with a specific state of the user. The guide unit guides the user to the specific state. A reference to be used for association with the specific state by the association unit is calibrated by using the biological information, the biological information being acquired from the user who is guided to the specific state by the guide unit.

BRIEF DESCRIPTION OF THE DRAWINGS

An exemplary embodiment of the present disclosure will be described in detail based on the following figures, wherein:

FIG. 4 is a block diagram illustrating an example functional configuration of the user terminal;

FIG. 7 is a flowchart illustrating an example association process procedure performed by a state association unit;

FIGS. 8A to 8D illustrate an example of calibration of reference brain waves; and FIGS. 9A to 9E illustrate example transitions of screens displayed on the user terminal during calibration of reference brain waves.

DETAILED DESCRIPTION

The following describes an exemplary embodiment of the present disclosure in detail with reference to the accompanying drawings.

Overall System Configuration

Figure 1:
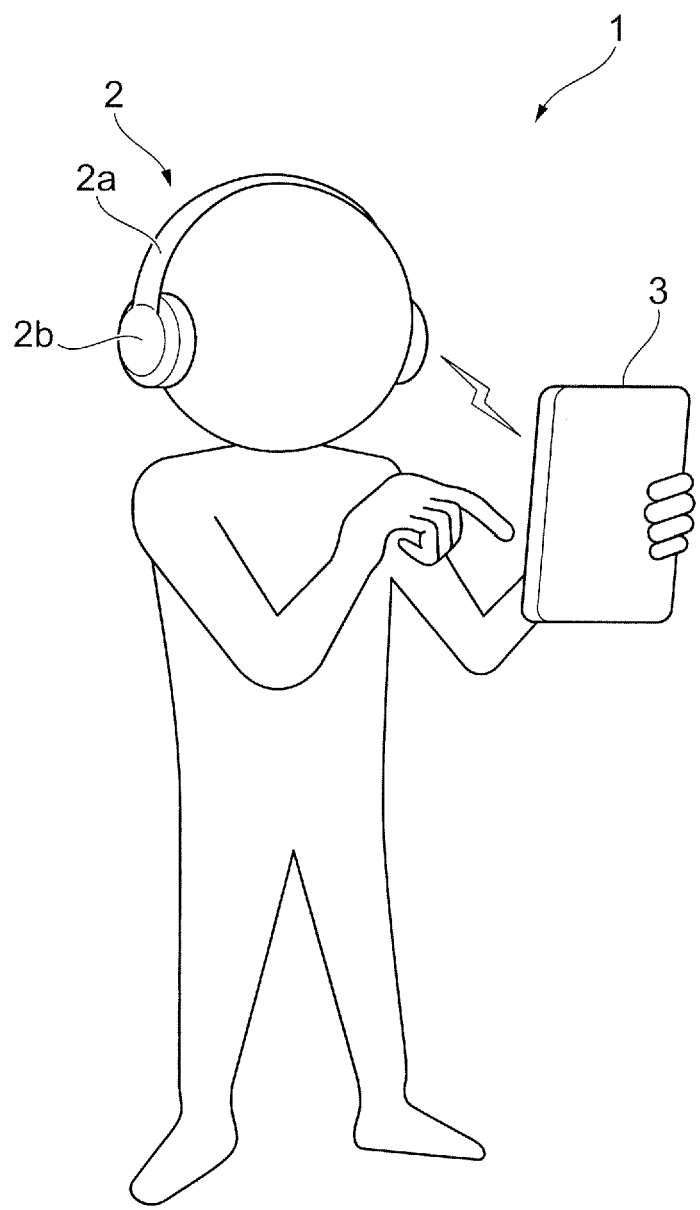
FIG. 1 illustrates an example overall configuration of a brain wave measurement system according to this exemplary embodiment.

First, an overall configuration of a brain wave measurement system 1 according to this exemplary embodiment will be described. FIG. 1 illustrates an example overall configuration of the brain wave measurement system 1 according to this exemplary embodiment.

As illustrated in FIG. 1, the brain wave measurement system 1 includes a brain wave measurement device 2 and a user terminal 3. The brain wave measurement device 2 measures (senses) brain waves of a user, and the user terminal 3 accepts an operation performed by the user. In this exemplary embodiment, the brain wave measurement system 1 is used as an example of an information processing system. The user terminal 3 is used as an example of an information processing apparatus.

The brain wave measurement device 2 and the user terminal 3 communicate with each other via wireless connection. More specifically, the brain wave measurement device 2 and the user terminal 3 are paired by Bluetooth (registered trademark) and communicate with each other. However, the brain wave measurement device 2 and the user terminal 3 may perform communication using any wireless communication technique other than a Bluetooth-based technique. Alternatively, the brain wave measurement device 2 and the user terminal 3 may communicate with each other via wired connection.

For example, the brain wave measurement device 2 has an earphone (or headphone) shape and is mounted on the head of the user whose brain waves are to be measured. In the illustrated example, the brain wave measurement device 2 includes a headband 2a and ear pads 2b. The headband 2a supports the brain wave measurement device 2 when worn on the head of the user. The ear pads 2b cover the ears of the user. The headband 2a and the ear pads 2b keep the brain wave measurement device 2 in contact with the user in such a manner that the user wearing the brain wave measurement device 2 is movable.

The brain wave measurement device 2 transmits information on the measured brain waves to the user terminal 3 via wireless communication. The brain waves are measured as potential information detected by electrodes 21 described below (see FIG. 2) (i.e., as potential information for measuring brain waves).

The user terminal 3 is a terminal apparatus that accepts an operation performed by the user. Examples of the user terminal 3 include portable information terminals such as a tablet computer and a smartphone. The user terminal 3 receives brain wave information of the user from the brain wave measurement device 2. Then, the user terminal 3 performs a process for associating the received brain wave information with a specific state of the user.

More specifically, a reference for associating the brain wave information received from the brain wave measurement device 2 with a specific state of the user is set in the user terminal 3. This reference is a reference of brain waves and is hereinafter referred to as reference brain waves. The specific state is, for example, a specific feeling experienced by the user. Specific examples of the specific state include a state in which the user is under normal conditions (hereinafter referred to as a "normal state"), a state in which the user is relaxed (hereinafter referred to as a "relaxed state"), and a state in which the user is concentrated (hereinafter referred to as a "concentrated state"). Reference brain waves are set for each of the multiple specific states.

The user terminal 3 compares the received brain wave information with reference brain waves that are set for each specific state and determines in which state the user is (i.e., in which state among the normal state, the relaxed state, and the concentrated state the user is). Upon determining the state of the user, the user terminal 3 displays a determination result on a display or the like of the user terminal 3 to present the determination result to the user. Further, the user terminal 3 transmits music data to the brain wave measurement device 2 on the basis of the determination result.

Further, the user terminal 3 performs a process for calibrating reference brain waves. Note that since biological information such as brain waves differs in individuals, it is necessary that biological information be calibrated for each individual user when the biological information is used. Additionally, the patterns of brain waves of each user may change in accordance with where the brain wave measurement device 2 is worn, the environment experienced by the user, or any other factor.

Accordingly, the user operates the user terminal 3 to calibrate reference brain waves. More specifically, the user follows instructions given on the screen of the user terminal 3 to calibrate reference brain waves on the basis of information on the brain waves of the user.

Examples of the normal state of the user, described above, include the calm state of mind experienced by the user. The calm state of mind experienced by the user is a state of mind causing no fluctuations of emotions. Specific examples of the calm state of mind experienced by the user include a state in which the user is at rest with the eyes open (a state in which the user is not moving and is kept calm). Other examples of the calm state of mind experienced by the user may include a state in which the user is at rest with the eyes closed.

In this exemplary embodiment, examples of the specific state of the user are not limited to the normal state, the relaxed state, and the concentrated state described above. Calmness, relaxation, and concentration are examples of a specific feeling experienced by the user. Other examples of the specific feeling experienced by the user include happiness, sadness, anger, fear, and surprise.

The specific state of the user may be a state not related to emotions of the user. Examples of such a specific state of the user include the state of fatigue, the state of hunger, and the state of drowsiness of the user.

In this exemplary embodiment, furthermore, brain waves are used as a non-limiting example of biological information. This exemplary embodiment may be applicable to any other biological information. Biological information is information generated from a living body such as the body of a human or any other animal. This exemplary embodiment is applicable to information that is biological information and that is associable with a specific state of a living body. Examples of the biological information to which this exemplary embodiment is applicable, other than brain waves, include vein (blood flow), heart rate, facial expression, pulse waves, voiceprint, sweat, action potentials (muscle currents or bioelectric currents), electrocardiogram, and blood pressure.

Configuration of Brain Wave Measurement Device

Figure 2:
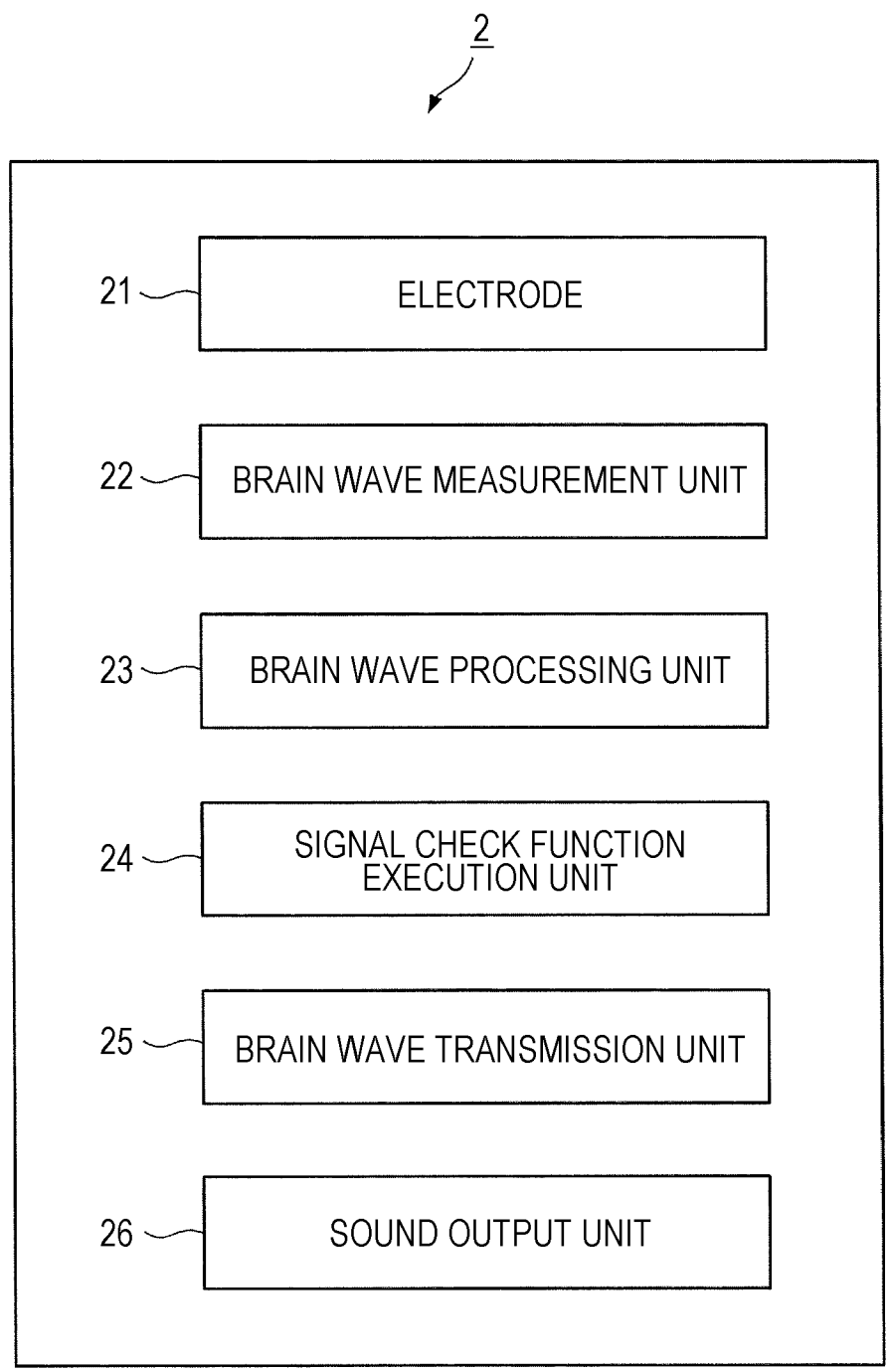
FIG. 2 illustrates an example configuration of a brain wave measurement device.

The configuration of the brain wave measurement device 2 will now be described. FIG. 2 illustrates an example configuration of the brain wave measurement device 2. As illustrated in FIG. 2, the brain wave measurement device 2 includes electrodes 21, a brain wave measurement unit 22, a brain wave processing unit 23, a signal check function execution unit 24, a brain wave transmission unit 25, and a sound output unit 26.

The electrodes 21 detect potential information of brain waves. For example, the electrodes 21 are disposed at a plurality of positions at which brain waves of the user wearing the brain wave measurement device 2 are easily measured.

For example, the brain wave measurement unit 22 amplifies potential differences between two of the electrodes 21 and measures the potential differences as brain waves. The brain waves measured by the brain wave measurement unit 22 are output to the brain wave processing unit 23. In this exemplary embodiment, brain waves are measured using a non-specific method and may be measured using an existing method.

The brain wave processing unit 23 performs a predetermined process on the brain waves output from the brain wave measurement unit 22. Examples of the predetermined process include various processes such as a process for removing noise from a brain wave signal and shaping a waveform and a process for further amplifying the brain wave signal. The brain waves processed by the brain wave processing unit 23 are output to the brain wave transmission unit 25. The brain waves measured by the brain wave measurement unit 22 may be output directly to the brain wave transmission unit 25 without being processed by the brain wave processing unit 23.

The signal check function execution unit 24 executes a signal check function when, for example, the brain wave measurement device 2 is started or before reference brain waves are calibrated. The signal check function is performed in order to determine whether brain waves are measurable, or, in other words, in order to determine whether the brain wave measurement unit 22 is capable of correctly measuring brain waves. Note that the signal check function is not intended to regulate differences between users, as in the calibration of reference brain waves, but is intended to examine and regulate an error caused by the device (the brain wave measurement device 2) due to a loose connection, malfunctioning of the device, or any other factor.

The brain wave transmission unit 25 transmits brain wave information output from the brain wave processing unit 23 to the user terminal 3.

The sound output unit 26 outputs sound to the outside. For example, the sound output unit 26 emits music to the user on the basis of music data received from the user terminal 3.

Hardware Configuration of User Terminal

Figure 3:
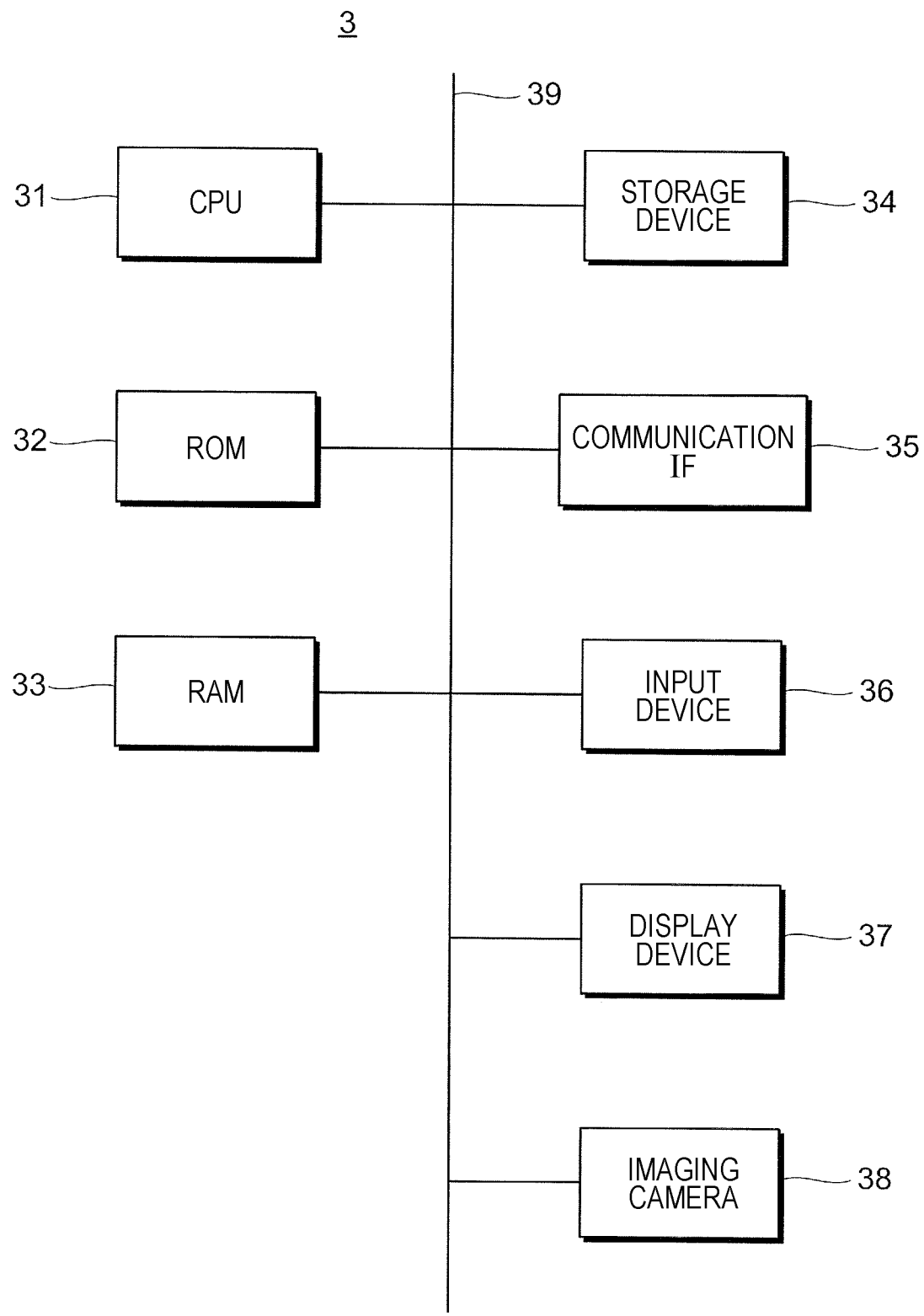
FIG. 3 illustrates an example hardware configuration of a user terminal.
Figure 5A:
FIGS. 5A to 5F illustrate example brain waves determined to occur by using a signal check function.
Figure 5C:
Figure 5E:
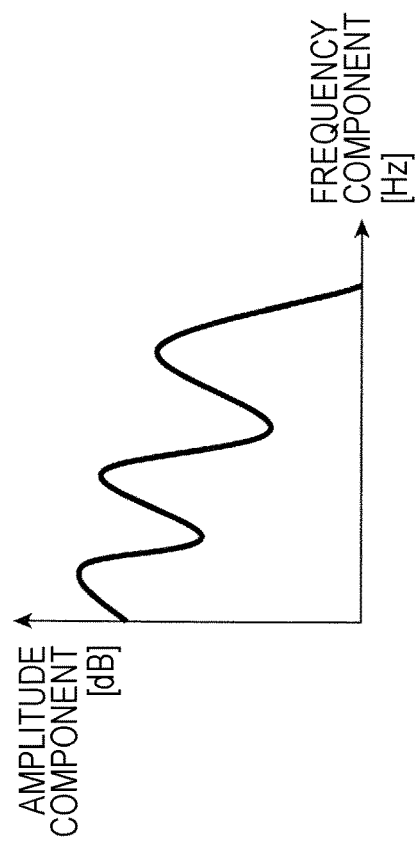
Figure 5B:
Figure 5D:
Figure 5F:
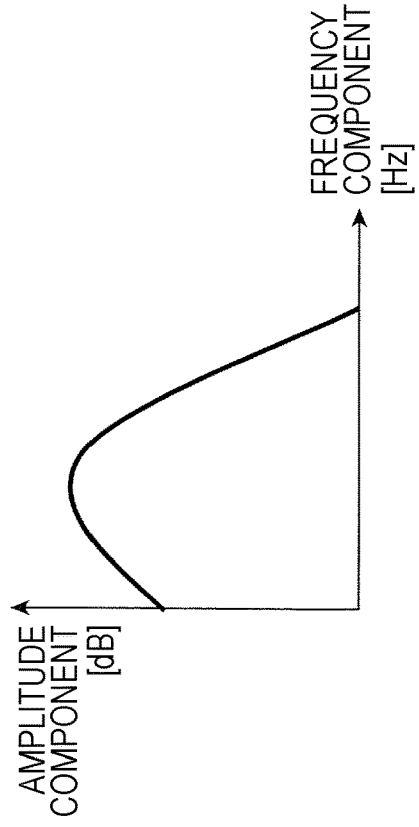

The hardware configuration of the user terminal 3 will now be described. FIG. 3 illustrates an example hardware configuration of the user terminal 3.

The user terminal 3 includes a central processing unit (CPU) 31, a read only memory (ROM) 32, and a random access memory (RAM) 33. The CPU 31 executes firmware or an application program to provide various functions. The ROM 32 is a storage area that stores firmware or a basic input output system (BIOS). The RAM 33 is an area where a program is executed.

The user terminal 3 further includes a non-volatile storage device 34, a communication interface (communication IF) 35, an input device 36 such as a touch panel, a display device 37, and an imaging camera 38. The storage device 34 stores a downloaded application program and so on. The communication IF 35 is used for external communication. The display device 37 includes a display and so on to be used to display information. The storage device 34 is implemented as, for example, a semiconductor memory.

The CPU 31 is connected to the various devices via a bus 39.

Functional Configuration of User Terminal

The functional configuration of the user terminal 3 will now be described. FIG. 4 is a block diagram illustrating an example functional configuration of the user terminal 3. As illustrated in FIG. 4, the user terminal 3 includes an operation acceptance unit 301, a display control unit 302, a brain wave information acquisition unit 303, a state association unit 304, a reference brain wave calibration unit 305, and a reference brain wave storage unit 306.

The operation acceptance unit 301 accepts an operation performed by the user. For example, the operation acceptance unit 301 accepts an operation of calibrating reference brain waves.

The brain wave information acquisition unit 303 is an example of an acquisition unit. The brain wave information acquisition unit 303 acquires, from the brain wave measurement device 2, brain wave information indicating brain waves of the user, which are measured by the brain wave measurement device 2.

The state association unit 304 is an example of an association unit. The state association unit 304 performs a process for associating the brain wave information acquired by the brain wave information acquisition unit 303 with a specific state of the user. Here, the state association unit 304 compares the brain wave information acquired by the brain wave information acquisition unit 303 with reference brain waves that are set for each specific state and determines in which state the user is. Then, the state association unit 304 transmits music data to the brain wave measurement device 2 on the basis of an association result obtained by the state association unit 304 (i.e., a determination result indicating in which state the user is).

More specifically, for example, upon determining that the user is in the relaxed state, the state association unit 304 transmits data of music presumably having a relaxing effect to the brain wave measurement device 2 via wireless communication in order to keep the user in the relaxed state (or in order to further relax the user).

The display control unit 302 is an example of a guide unit. The display control unit 302 generates a control signal for controlling the display of the display device 37 and controls the display of the display device 37.

For example, the display control unit 302 displays an association result obtained by the state association unit 304 (a determination result indicating in which state the user is).

Further, for example, the display control unit 302 displays an operation screen for calibrating reference brain waves. The operation screen for calibrating reference brain waves includes a screen for guiding the user to a specific state (hereinafter referred to as a "guide screen"), which will be described in detail below. The display control unit 302 displays the guide screen on the display device 37 to guide the user to a specific state (e.g., the normal state, the relaxed state, or the concentrated state).

The reference brain wave calibration unit 305 is an example of a calibration unit. The reference brain wave calibration unit 305 performs a process for calibrating reference brain waves. When a predetermined condition is satisfied, the reference brain wave calibration unit 305 calibrates reference brain waves. The predetermined condition is satisfied when, for example, calibration is estimated to be required. Specifically, for example, when the brain wave measurement device 2 is started or when an application program for brain wave measurement is started, the predetermined condition is satisfied. Also, for example, when an association process performed by the state association unit 304 fails or when a certain period (e.g., one month) has elapsed since the last time calibration was performed, the predetermined condition is satisfied. For example, calibration may be triggered by an instruction given by the user.

In the calibration of reference brain waves, as described above, a guide screen is displayed. Then, the reference brain wave calibration unit 305 calibrates reference brain waves by using brain wave information acquired from the user who is guided to a specific state.

Before the reference brain wave calibration unit 305 performs calibration, the signal check function is executed. After the signal check function determines that no error has occurred, or, in other words, after it is confirmed that the brain wave information acquisition unit 303 correctly acquires brain wave information, reference brain waves are calibrated.

The reference brain wave storage unit 306 stores reference brain waves that are set for each specific state of the user. The stored reference brain waves are reference brain waves calibrated by the reference brain wave calibration unit 305. Alternatively, preset values are stored, for example. The preset values are initial values determined in advance as values common to all users.

The functional units included in the user terminal 3 illustrated in FIG. 4 are implemented by cooperation of software and hardware resources. Specifically, for example, when the user terminal 3 is implemented by the hardware configuration illustrated in FIG. 3, the application program for brain wave measurement or the like, which is stored in the ROM 32 or the storage device 34, is read into the RAM 33 and is executed by the CPU 31 to implement the operation acceptance unit 301, the display control unit 302, the brain wave information acquisition unit 303, the state association unit 304, the reference brain wave calibration unit 305, and so on. The reference brain wave storage unit 306 is implemented by, for example, the storage device 34.

Description of Brain Waves

Brain waves that are measured by the brain wave measurement device 2 will now be described.

Focusing on brain wave frequencies, brain waves are typically categorized into five components, namely, gamma ($\gamma$) waves, beta ($\beta$) waves, alpha ($\alpha$) waves, theta ($\theta$) waves, and delta ($\delta$) waves.

The γ waves are oscillations with frequencies greater than or equal to 30 Hz and are said to appear in highly anxious or excited conditions.

The β waves are oscillations with frequencies in a range of 30 to 13 Hz and are said to appear in nervous conditions or under stress.

The α waves are oscillations with frequencies in a range of 13 to 8 Hz and are said to appear in calm (relaxed) conditions or with eyes closed.

The θ waves are oscillations with frequencies in a range of 8 to 4 Hz and are said to appear in deeply relaxed conditions or in sleeping states.

The δ waves are oscillations with frequencies less than 4 Hz and are said to appear during deep sleep or coma.

In actuality, these five components are combined to form a brain wave pattern. In some cases, the γ waves are identified as the β waves.

In the description given herein, brain waves are categorized into five (or four) components on the basis of brain wave frequencies. However, this categorization is an example. In this exemplary embodiment, brain waves may not necessarily be categorized in the way described above, and any other standard may be used to categorize brain waves into components.

Description of Signal Check Function

The signal check function will now be described. FIGS. 5A to 5F illustrate example brain waves determined to occur by using the signal check function. The signal check function execution unit 24 determines whether an error has occurred for items for the signal check function, for example, items relating to a brain wave signal, such as the flatness of the brain wave signal, the magnitude of the amplitude of the brain wave signal, or the ratio of frequencies in the brain wave signal.

First, examination of the item for the flatness of the brain wave signal will be described. In this case, whether an error has occurred is determined by using a threshold, examples of which include a threshold on the amplitude (threshold 1) and a threshold on the number of waves (threshold 2). For example, if the number of amplitudes exceeding the threshold 1 is smaller than the threshold 2 in brain waves for a certain period of time, the brain waves are excessively flat and an error occurs. For example, in the brain waves illustrated in FIG. 5A, the number of amplitudes exceeding the threshold 1 is larger than the threshold 2, and thus it is determined that the brain waves are normal. In the brain waves illustrated in FIG. 5B, in contrast, the number of amplitudes exceeding the threshold 1 is smaller than the threshold 2, and thus it is determined that an error has occurred.

Next, examination of the item for the magnitude of the amplitude of the brain wave signal will be described. In this case, whether an error has occurred is determined by using a threshold, examples of which include a threshold indicating the upper limit of amplitude (threshold 3). For example, if brain waves for a certain period of time have an amplitude exceeding the threshold 3, the amplitude is excessively large and an error occurs. For example, in the brain waves illustrated in FIG. 5C, there is no amplitude exceeding the threshold 3, and thus it is determined that the brain waves are normal. In contrast, the brain waves illustrated in FIG. 5D have an amplitude exceeding the threshold 3, and thus it is determined that an error has occurred.

Next, examination of the item for the ratio of frequencies in the brain wave signal will now be described. In this case, whether an error has occurred is determined by using a threshold, examples of which include a threshold on steepness (threshold 4). Then, for example, the frequency component (in hertz) and the amplitude component (in decibels) are extracted from brain waves for a certain period of time. If the steepness exceeds the threshold 4, an error occurs. For example, in the brain waves illustrated in FIG. 5E, the steepness does not exceed the threshold 4, and thus it is determined that the brain waves are normal. In the brain waves illustrated in FIG. 5F, in contrast, the steepness exceeds the threshold 4, and thus it is determined that an error has occurred.

The signal check function may be performed on brain waves including a combination of the five components or may be performed on one or more of the five components.

In the way described above, the signal check function execution unit 24 compares brain wave information measured from the user with the thresholds for the various items and determines whether an error has occurred. If an error has occurred, it is determined that the brain wave measurement unit 22 fails to measure brain waves correctly. Then, the signal check function execution unit 24 notifies the user terminal 3 that an error has occurred, or, in other words, that the correct measurement of brain waves by the brain wave measurement unit 22 is not confirmed. As a result, the display control unit 302 of the user terminal 3 displays a message provided from the signal check function execution unit 24 (or a notification indicating that the acquisition of brain waves by the brain wave information acquisition unit 303 is not confirmed) on the display device 37 and provides a notification to the user.

The thresholds for the various items are determined in advance as initial values or are determined as values that can be set or changed by the user.

The items for the signal check function are not limited to the items described above for parameters of a brain wave signal. For example, the signal check function execution unit 24 may check the magnitude of the resistance of the electrodes 21. In this case, the signal check function execution unit 24 determines that an error has occurred when, for example, the magnitude of the resistance is larger than a predetermined upper limit or when the magnitude of the resistance is smaller than a predetermined lower limit.

Procedure of Process for Calibrating Reference Brain Waves

Figure 6:
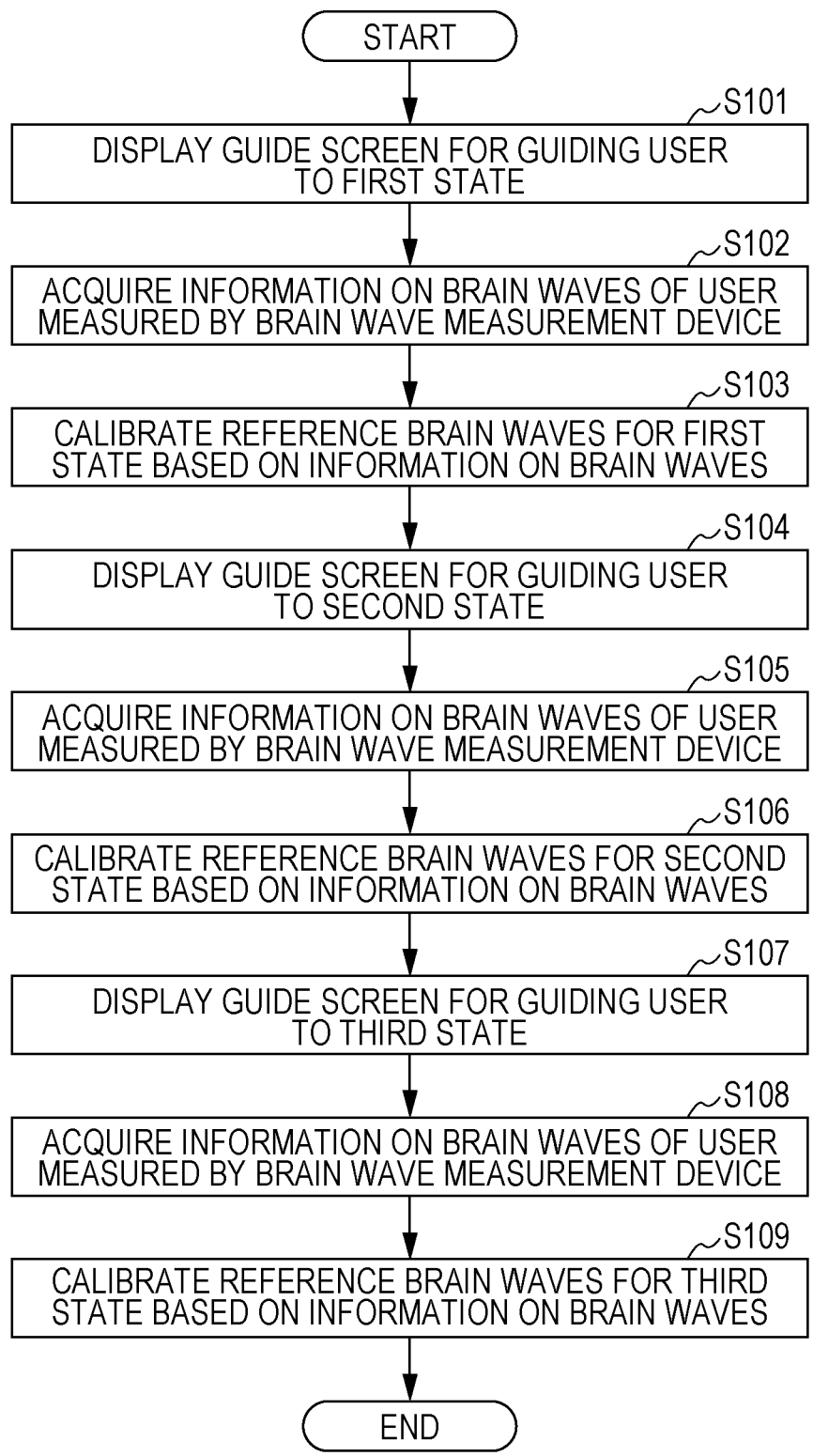
FIG. 6 is a flowchart illustrating an example process procedure in which the user terminal calibrates reference brain waves.

A procedure of a process for calibrating reference brain waves will now be described. FIG. 6 is a flowchart illustrating an example process procedure in which the user terminal 3 calibrates reference brain waves. In the illustrated example, the user is guided to a first state, a second state, and a third state in this order, and calibration is assumed to be performed. For example, the first state, the second state, and the third state are the normal state, the relaxed state, and the concentrated state, respectively.

First, the process for calibrating reference brain waves is started after the signal check function determines that no error has occurred. Then, the display control unit 302 displays a guide screen for guiding the user to the first state (step S101). The brain wave information acquisition unit 303 acquires information on brain waves of the user, which are measured by the brain wave measurement device 2 (step S102). Further, the reference brain wave calibration unit 305 calibrates reference brain waves for the first state on the basis of the acquired information on the brain waves (step S103).

Then, after a certain period of time (e.g., 5 seconds) has elapsed since the guide screen for guiding the user to the first state was displayed, the display control unit 302 displays a guide screen for guiding the user to the second state (step S104). In this case, as in step S102, the brain wave information acquisition unit 303 acquires information on brain waves of the user, which are measured by the brain wave measurement device 2 (step S105). Further, the reference brain wave calibration unit 305 calibrates reference brain waves for the second state on the basis of the acquired information on the brain waves (step S106).

Then, after a certain period of time (e.g., 5 seconds) has elapsed since the guide screen for guiding the user to the second state was displayed, the display control unit 302 displays a guide screen for guiding the user to the third state (step S107). In this case, as in steps S102 and S105, the brain wave information acquisition unit 303 acquires information on brain waves of the user, which are measured by the brain wave measurement device 2 (step S108). Further, the reference brain wave calibration unit 305 calibrates reference brain waves for the third state on the basis of the acquired information on the brain waves (step S109). Then, the process flow ends.

Procedure of Association Process

The procedure of the association process performed by the state association unit 304 will now be described. FIG. 7 is a flowchart illustrating an example procedure of the association process performed by the state association unit 304.

First, the brain wave information acquisition unit 303 acquires information on brain waves of the user, which are measured by the brain wave measurement device 2, from the brain wave measurement device 2 (step S201). Then, the state association unit 304 compares the acquired information on the brain waves with reference brain waves stored in the reference brain wave storage unit 306 (reference brain waves that are set for each specific state) (step S202). Then, the state association unit 304 performs a process for associating the acquired information on the brain waves with the specific state (step S203). For example, if the comparison result obtained in step S202 determines that the acquired information on the brain waves corresponds to brain waves for the relaxed state, the state association unit 304 performs a process for associating the acquired information on the brain waves with the relaxed state.

Then, the state association unit 304 transmits music data to the brain wave measurement device 2 on the basis of the association result obtained by the state association unit 304 (step S204). For example, when a process for associating the acquired information on the brain waves with the relaxed state is performed, the state association unit 304 transmits data of music presumably having a relaxing effect to the brain wave measurement device 2. In the brain wave measurement device 2, accordingly, the sound output unit 26 emits music to the user. Then, the process flow ends.

Description of Calibration of Reference Brain Waves

The calibration of reference brain waves will now be described. FIGS. 8A to 8D illustrate examples of the calibration of reference brain waves. In FIGS. 8A to 8D, brain wave patterns of different users are illustrated. Specifically, FIGS. 8A to 8D illustrate brain wave patterns measured from users A to D, respectively, and, for each of the users A to D, brain waves for the normal state, brain waves for the relaxed state, and brain waves for the concentrated state are illustrated. In FIGS. 8A to 8D, the vertical axis represents the amplitude of brain waves, in μV, and the horizontal axis represents time.

The reference brain wave calibration unit 305 calculates, for brain waves of each user for each state, an average amplitude value of brain waves for a certain period of time. For example, the reference brain wave calibration unit 305 calculates, for the brain wave patterns of the user A illustrated in FIG. 8A, an average amplitude value of brain waves for a certain period of time for each of the normal state, the relaxed state, and the concentrated state. As a result of the calculation, the average amplitude values are 10 μV for the normal state, 30 μV for the relaxed state, and 50 μV for the concentrated state, for example.

The average amplitude values are also calculated for the other users in a similar way. As a result of the calculation, for the user B, the average amplitude values are 5 μV for the normal state, 15 μV for the relaxed state, and 25 μV for the concentrated state, for example. For the user C, the average amplitude values are 10 μV for the normal state, 50 μV for the relaxed state, and 60 μV for the concentrated state, for example. For the user D, the average amplitude values are 5 μV for the normal state, 25 μV for the relaxed state, and 45 μV for the concentrated state, for example.

Note that the brain waves of the user B tend to entirely have a smaller amplitude than the brain waves of the user A. Further, the brain waves of the user C tend to have approximately the same amplitude as the brain waves of the user A in the normal state, but tend to have a larger amplitude in the relaxed state and the concentrated state. Further, the brain waves of the user D tend to entirely have a smaller amplitude than the brain waves of the user A, but differences in amplitude between states (e.g., differences between the normal state and the relaxed state) are almost the same as those of the brain waves of the user A.

In this manner, brain waves acquired from users differ from one user to another, and thus calibration is performed on a user-by-user basis.

For example, in the calibration of reference brain waves based on an average amplitude value, an average value for each state is used as the amplitude of the reference brain waves for the state. For example, in the case of the user A, the average amplitude value (10 μV) for the normal state is used as the amplitude of the reference brain waves for the normal state. Likewise, the average amplitude value (30 μV) for the relaxed state is used as the amplitude of the reference brain waves for the relaxed state. Further, the average amplitude value (50 μV) for the concentrated state is used as the amplitude of the reference brain waves for the concentrated state. The state association unit 304 performs association using the reference brain waves calibrated in the way described above.

For example, the state association unit 304 associates the acquired information on the brain waves with a state corresponding to the closest reference brain waves among the reference brain waves for the respective states. For example, the amplitude of the brain waves of the user A acquired by the brain wave information acquisition unit 303 is 25 μV. The amplitude of the reference brain waves that is closest to 25 μV among the reference brain waves for the respective states is 30 μV (the reference brain waves for the relaxed state). Thus, the state association unit 304 associates the acquired information on the brain waves with the relaxed state.

Alternatively, for example, the state association unit 304 may perform association based on a certain amplitude range relative to the amplitude of the reference brain waves for each state.

For example, in the case of the user A, the amplitude of the reference brain waves for the normal state is 10 μV, the amplitude of the reference brain waves for the relaxed state is 30 μV, and the amplitude of the reference brain waves for the concentrated state is 50 μV. In this case, the difference in amplitude between the normal state and the relaxed state is 20 μV, and the difference in amplitude between the normal state and the concentrated state is 20 μV. Thus, an amplitude range of 10 μV above and below the amplitude of the reference brain waves for each state is determined. Specifically, an amplitude range of 0 to 20 μV is determined for the normal state, an amplitude range of 20 to 40 μV is determined for the relaxed state, and an amplitude range of 40 to 60 μV is determined for the concentrated state. For example, when the amplitude of the brain waves of the user A, which are acquired by the brain wave information acquisition unit 303, is 45 μV, the state association unit 304 associates the acquired information on the brain waves with the concentrated state.

For example, in the case of the user C, the amplitude of the reference brain waves for the normal state is 10 μV, the amplitude of the reference brain waves for the relaxed state is 50 μV, and the amplitude of the reference brain waves for the concentrated state is 60 μV. In this case, the difference in amplitude between the normal state and the relaxed state is 40 μV, and the difference in amplitude between the normal state and the concentrated state is 50 μV. Thus, unlike the user A, for example, an amplitude range of 0 to 45 μV is determined for the normal state, an amplitude range of 45 μV to 55 μV is determined for the relaxed state, and an amplitude range of 55 to 65 μV is determined for the concentrated state.

As described above, a certain amplitude range used for association with each state is determined for each user on the basis of the amplitude in the normal state. Note that certain amplitude ranges used for association with other states are determined based on the amplitude in the normal state by using differences between the reference brain waves for the normal state and the reference brain waves for the other states. Note that a plurality of states are based on the normal state, by way of example, and are not necessarily based on the normal state.

The reference brain wave calibration unit 305 may calibrate reference brain waves by using one or more of the five components of brain waves described above or by using brain waves including a combination of the five components. For example, when the reference brain wave calibration unit 305 calibrates reference brain waves by using one of the five components (e.g., α waves), the state association unit 304 also performs association by using information on brain waves of that component (i.e., α waves). For example, when the reference brain wave calibration unit 305 calibrates reference brain waves by using brain waves including a combination of the five components, the state association unit 304 also performs association by using information on brain waves including a combination of the five components.

Moreover, which component of brain waves strongly appears may depend on the specific state. Thus, which of the five components to use to perform calibration or association may differ in accordance with the specific state. For example, only α waves may be used to perform calibration and association for the relaxed state of the user, and β waves may be used to perform calibration and association for the concentrated state of the user.

When only one or more of the five components are used for association or calibration, either the user terminal 3 or the brain wave measurement device 2 may perform a process for extracting one or more components from brain waves including a combination of the five components.

While the example described above describes calibration of reference brain waves whose amplitude is an average amplitude value for each state, calibration of reference brain waves is not limited to that described above. For example, reference brain waves whose amplitude is a peak amplitude for each state may be calibrated. Alternatively, for example, the value of the variance of amplitudes may be used as the amplitude of the reference brain waves, and association may be performed in accordance with the degree of the variation of the amplitudes.

Alternatively, any parameter of brain waves, other than the amplitude of brain waves, may be used for calibration. Examples of the other parameter include the wavelength, frequency, and cycle of brain waves. Alternatively, for example, the rate of occurrence of a certain brain wave component such as α waves may be used for calibration.

Screen Transition During Calibration of Reference Brain Waves

Next, transitions of screens displayed on the user terminal 3 during calibration of reference brain waves will be described. FIGS. 9A to 9E illustrate example transitions of screens displayed on the user terminal 3 during calibration of reference brain waves. In the illustrated examples, the user is guided to a plurality of specific states, namely, the normal state, the relaxed state, and the concentrated state, in this order, and brain waves of the user are measured for each of the states.

Figure 9A:
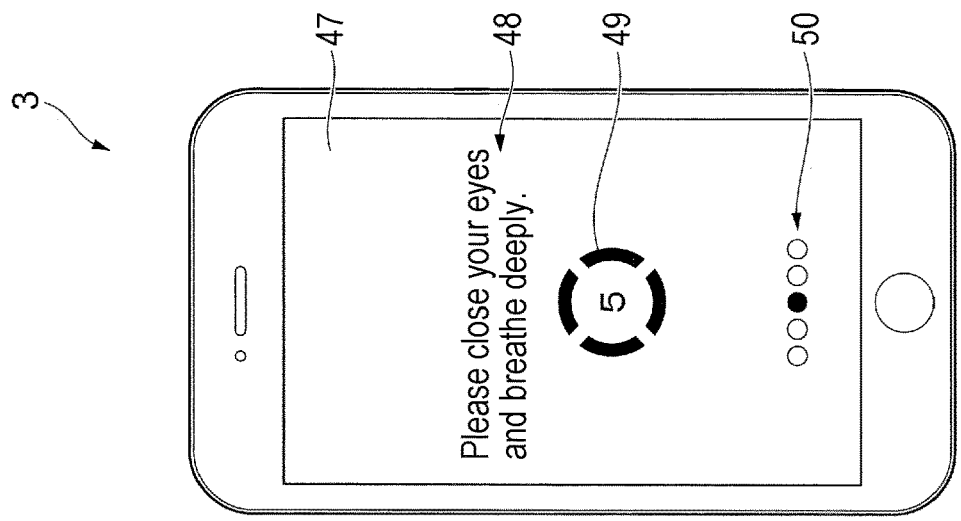

First, when the brain wave measurement device 2 is started or when the application program for brain wave measurement is started, as illustrated in FIG. 9A, an initial screen 41 for calibration is displayed. As described above, the initial screen 41 may be displayed when the user gives an instruction or when the association process fails. Before the initial screen 41 is displayed or during a period from when the initial screen 41 is displayed to when the user starts to be guided to a specific state, the signal check function is executed to check whether the brain wave information acquisition unit 303 correctly acquires brain wave information.

Here, if no Bluetooth-based connection is identified between the brain wave measurement device 2 and the user terminal 3, the user terminal 3 may display a screen for prompting the user to check their Bluetooth-based connection.

As illustrated in FIG. 9A, the initial screen 41 provides a description of an application program for brain wave measurement. The initial screen 41 also indicates that calibration is started. Further, the number of screens currently in use for calibrating reference brain waves is shown by a row of dots in a region 42, with the dot representing the current screen highlighted. The example illustrated in FIG. 9A indicates that the current screen is the first out of five screens.

For example, when the user makes a gesture such as flicking or tapping on the initial screen 41, a transition occurs to the next screen. The next screen is a normal-state guide screen 43 illustrated in FIG. 9B. The normal-state guide screen 43 is a guide screen for guiding the user to the normal state. More specifically, the message "Please take your eyes off this screen and breathe deeply with your eyes open" is displayed in a region 44. That is, the user takes their eyes off the normal-state guide screen 43 (or takes their eyes off the display of the display device 37) and breathes deeply with their eyes open, and the brain waves of the user during this operation are measured as brain waves in the normal state.

The guide for the user lasts for 5 seconds, for example. That is, the message "Please take your eyes off this screen and breathe deeply with your eyes open" is displayed for 5 seconds. The brain wave information acquisition unit 303 of the user terminal 3 acquires information on the brain waves of the user, which are measured by the brain wave measurement device 2 during the period of 5 seconds. The acquired information on the brain waves is used for calibration by the reference brain wave calibration unit 305 as brain waves in the normal state. The message "Please take your eyes off this screen and breathe deeply with your eyes open" may be provided audibly.

The remaining guide time (e.g., in seconds) is displayed in a region 45. The example illustrated in FIG. 9B indicates that the remaining guide time to the normal state is 5 seconds.

Further, as in the region 42 illustrated in FIG. 9A, the number of screens currently in use is shown by the row of dots in a region 46, with the dot representing the current screen highlighted. The illustrated example indicates that the current screen is the second out of the five screens.

Moreover, the reference brain wave calibration unit 305 performs calibration by using, as a reference, brain waves in the normal state among the plurality of specific states. Thus, the display control unit 302 displays a guide screen to the normal state, which is used as a reference, as an initial guide screen among a plurality of guide screens. Guiding the user initially to a reference state clearly identifies the difference from the reference state when the user is guided to another state, for example. As a result, it may be checked whether brain waves of the user who is guided to another state are correctly measured.

After the guide lasts for 5 seconds on the normal-state guide screen 43, a transition occurs to the next screen. The next screen is a relaxed-state guide screen 47 illustrated in FIG. 9C. The relaxed-state guide screen 47 is a guide screen for guiding the user to the relaxed state. More specifically, the message "Please close your eyes and breathe deeply" is displayed in a region 48. That is, the user closes their eyes and breathes deeply, and the brain waves of the user during this operation are measured as brain waves in the relaxed state. The message "Please close your eyes and breathe deeply" may be provided audibly.

The guide for the user lasts for 5 seconds, for example, as in the normal state. That is, the message "Please close your eyes and breathe deeply" is displayed for 5 seconds. The brain wave information acquisition unit 303 of the user terminal 3 acquires information on brain waves of the user, which are measured by the brain wave measurement device 2 during the period of 5 seconds. The acquired information on the brain waves is used for calibration by the reference brain wave calibration unit 305 as brain waves in the relaxed state.

Figure 9B:
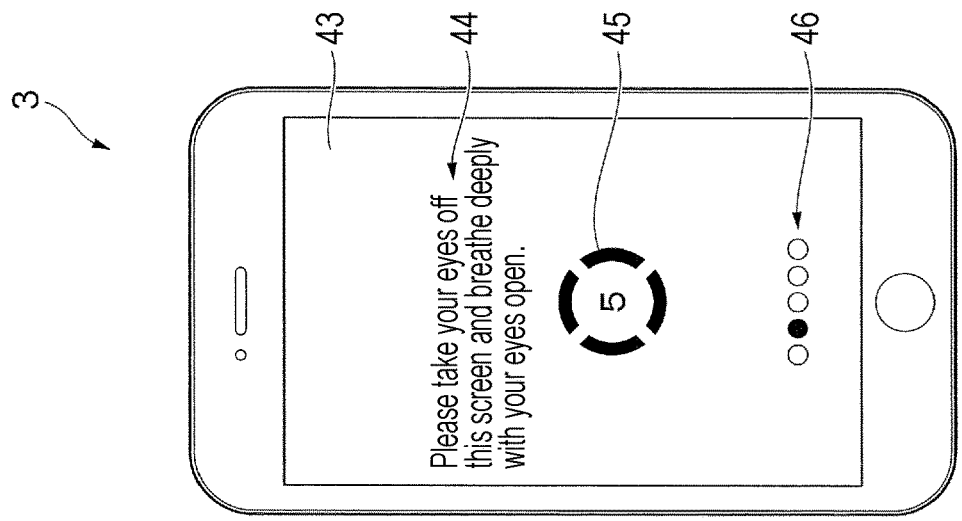
Figure 9C:
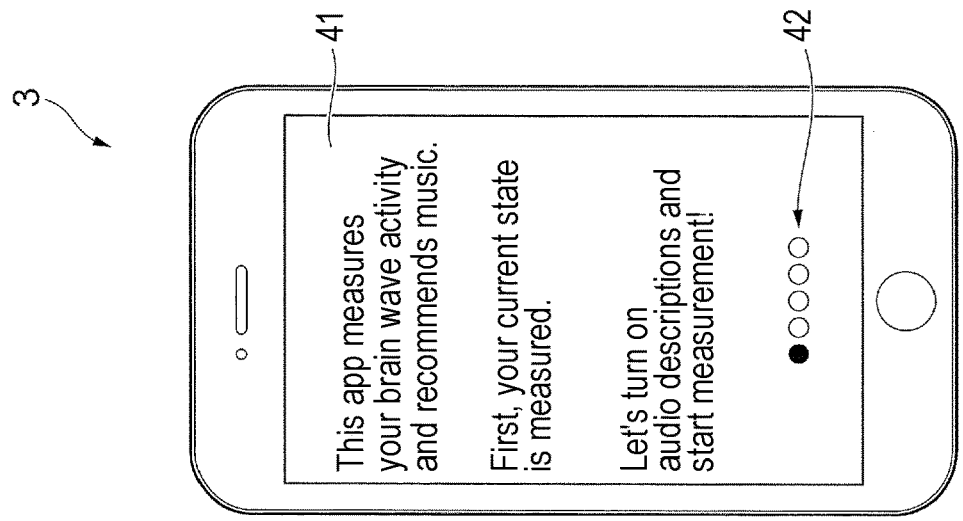

As in the region 45 illustrated in FIG. 9B, the remaining guide time (e.g., in seconds) is displayed in a region 49.

Further, as in the region 42 illustrated in FIG. 9A, the number of screens currently in use is shown by the row of dots in a region 50, with the dot representing the current screen highlighted. The illustrated example indicates that the current screen is the third out of the five screens.

After the guide lasts for 5 seconds on the relaxed-state guide screen 47, a transition occurs to the next screen. The next screen is a concentrated-state guide screen 51 illustrated in FIG. 9D. The concentrated-state guide screen 51 is a guide screen for guiding the user to the concentrated state. More specifically, the message "Please stare at a number inside the circle" is displayed in a region 52. That is, the user stares at a number shown in a region 53, and the brain waves of the user during this operation are measured as brain waves in the concentrated state. The message "Please stare at a number inside the circle" may be provided audibly.

As in the region 45 illustrated in FIG. 9B, the remaining guide time (e.g., in seconds) is displayed in the region 53.

Further, as in the region 42 illustrated in FIG. 9A, the number of screens currently in use is shown by the row of dots in a region 54, with the dot representing the current screen highlighted. The illustrated example indicates that the current screen is the fourth out of the five screens.

After the guide lasts for 5 seconds on the concentrated-state guide screen 51, a transition occurs to the next screen. The next screen is a completion notification screen 55 illustrated in FIG. 9E. The completion notification screen 55 is a screen indicating that the guide of the user has been completed. As in FIG. 9E, the completion notification screen 55 shows a message indicating that the guide (i.e., the measurement of brain waves of the user) has been completed. Further, the description of further services available on the application program for brain wave measurement, such as visualizing the state of the user and playing music suitable for the state of the user, is provided. In addition, a message indicating a procedure for displaying the initial screen 41 again is displayed so that the user is able to give an instruction to retry calibration.

Further, as in the region 42 illustrated in FIG. 9A, the number of screens currently in use is shown by the row of dots in a region 56, with the dot representing the current screen highlighted. The illustrated example indicates that the current screen is the fifth out of the five screens, that is, the last screen.

In the way described above, the user is sequentially guided to a plurality of specific states, and brain waves of the user in each of the states are measured. Then, the reference brain wave calibration unit 305 performs calibration on the basis of information on the brain waves of the user in each of the states.

In the example described above, the guide to each of the normal state, the relaxed state, and the concentrated state lasts for 5 seconds, by way of example but not limitation. The guide to each state may last for a time longer or shorter than 5 seconds. In addition, the periods of time set to guide the user to the states may not all be the same, and an appropriate period of time may be set to guide the user to each of the states.

If an error occurs within 5 seconds during guiding, the user may be guided for another 5 seconds and then calibration may be performed.

In addition, for example, if the reference brain wave calibration unit 305 has not completed calibration after the lapse of 5 seconds while the user is being guided to a state, the display control unit 302 may continuously guide the user to the state until the reference brain wave calibration unit 305 completes calibration (or may continuously display a screen for guiding the user to the state). For example, if the reference brain wave calibration unit 305 completes calibration before the lapse of 5 seconds while the user is being guided to a state, the display control unit 302 may finish guiding the user to the state (or may change the screen for guiding the user to the state to the next screen).

In the example described above, furthermore, the user is guided to one state (reference brain waves in one state are calibrated) for 5 seconds, and is then guided to the next state (reference brain waves in the next state are calibrated), by way of example but not limitation. The user may be guided to one state and, after a certain time interval (e.g., 10 seconds), to the next state. Note that after a certain period of time has elapsed since the user was guided to one state (since reference brain waves in one state were calibrated), the display control unit 302 may start guiding the user to the next state (start calibrating reference brain waves in the next state).

Moreover, when the user is guided to one state and is then guided to the next state, it may take time for the user to change their state from the one state to the next state, and the user may be confused in the states. In this case, brain waves generated in the one state may be mixed with brain waves measured in the next state and may affect calibration of the reference brain waves in the next state. To address the mixture of brain waves, a certain time interval is provided between guiding the user to one state and guiding the user to the next state. This prevents the one state from affecting the measurement of brain waves in the next state and facilitates accurate measurement of brain waves in the next state.

Furthermore, the order in which the user is guided to a plurality of specific states may be set so as not to cause confusion in the states. For example, as a result of comparison between the relaxed state and the concentrated state, when brain waves generated in the relaxed state require time to disappear once they are generated, the user is guided to the concentrated state and is then guided to the relaxed state.

In the example described above, furthermore, calibration is performed for all of the normal state, the relaxed state, and the concentrated state. However, the reference brain wave calibration unit 305 may perform re-calibration only for a state that requires calibration of reference brain waves among these states. In this case, for example, the display control unit 302 may display only a guide screen to the state that requires calibration of reference brain waves in the calibration of reference brain waves, without displaying guide screens for the other states.

Examples of the state that requires calibration of reference brain waves include a state for which a certain period (e.g., one month) has elapsed since reference brain waves were previously calibrated, and a state among a plurality of specific states for which the number of times association has been performed is smaller than that for the other states.

As described above, in this exemplary embodiment, the display control unit 302 of the user terminal 3 displays a guide screen for guiding the user to a specific state to guide the user to the specific state. The reference brain wave calibration unit 305 of the user terminal 3 calibrates reference brain waves, which are used for association with a specific state, by using brain wave information acquired from the user who is guided to the specific state. In this way, the user follows instructions given on the screen of the user terminal 3, thereby allowing the user to calibrate reference brain waves.

In this exemplary embodiment, furthermore, a server device (not illustrated) that implements all or some of the functions of the user terminal 3 may be provided. In this case, the brain wave measurement device 2 and the server device communicate with each other via a network. For example, when the user accesses the server device by using the user terminal 3, the server device transmits information on a guide screen to the user terminal 3 and the guide screen is displayed on the user terminal 3. Further, for example, information on the brain waves measured by the brain wave measurement device 2 is transmitted to the server device, and the server device performs an association and calibration process. Further, for instance, the functions of the operation acceptance unit 301, the display control unit 302, and the brain wave information acquisition unit 303 may be implemented by the user terminal 3, and a calibration and association process, which is performed by the state association unit 304, the reference brain wave calibration unit 305, the reference brain wave storage unit 306, and so on, may be performed by the server device. In this case, the server device may be identified as an example of an information processing apparatus, or the server device and the user terminal 3 may be identified as an example of an information processing system.

Note that when the user terminal 3 implements the functional units illustrated in FIG. 4, information on brain waves measured from the user and reference brain waves is prevented from leaking outside the user terminal 3. In contrast, the functions of the user terminal 3 are implemented by the server device, thereby allowing the server device to collect information on brain waves measured from the user and reference brain waves such that the collected information is sharable by a plurality of users. In addition, the functions of the user terminal 3 are implemented by the server device, thereby reducing the load imposed on the user terminal 3.

Alternatively, the brain wave measurement device 2 may execute all or some of the functions of the user terminal 3. The brain wave measurement device 2 executes all or some of the functions of the user terminal 3, thereby, for example, reducing the load imposed on the user terminal 3 or reducing the time taken for the user to perform operations. Specifically, for example, the application program for brain wave measurement or the like is executed by a control unit (not illustrated) or the like of the brain wave measurement device 2, thereby allowing the brain wave measurement device 2 to implement the functions of the user terminal 3. The user provides, for example, voice input to the brain wave measurement device 2, instead of performing various operations on the screen of the user terminal 3, to give an instruction to the brain wave measurement device 2. In this case, the brain wave measurement device 2 may be identified as an example of an information processing apparatus.

For example, some of the functions of the brain wave measurement device 2, such as the signal check function, may be executed by the user terminal 3.

In the example described above, furthermore, the display control unit 302 displays a guide screen to guide the user to a specific state. However, any other technique may be used to guide the user to a specific state. For example, an audio message, such as "Please close your eyes and breathe deeply", instead of a displayed guide screen, may be provided from the user terminal 3 to guide the user to a specific state. Alternatively, a scent for guiding the user to a specific state, such as a scent presumably having a relaxing effect, may be released from the user terminal 3 to guide the user to a specific state. Additionally, any tool capable of guiding the user to a specific state by the use of the five senses of the user may be used as a guiding method.

In the example described above, furthermore, music is played on the basis of the association result obtained by the state association unit 304. The user terminal 3 may further acquire brain waves of the user who is listening to the music and may determine whether the user actually feels relaxed by the music. This determination assesses the relaxing effect of music. The next time music is played to make the user feel relaxed, the user terminal 3 may perform control to play music assessed to have a higher relaxing effect and not to play music assessed to have a lower relaxing effect. Such a feedback function is implemented by, for example, executing the application program for brain wave measurement. As an example of such a program, a deep learning program or a machine learning program may be used.

The relaxing effect is assessed on a user-by-user basis, and music assessed to have a higher relaxing effect and music assessed to have a lower relaxing effect are different from one user to another. It is expected that a plurality of users tend in common to feel relaxed to some extent while listening to music. Thus, the result of determination of whether listening to music has a relaxing effect may be shared by a plurality of users, and music may be played by using the determination result of other users.

A process using an association result is not limited to a process for playing music. The process using an association result is a process that appeals to the five senses of the user, for example. Examples of the process include playing music, displaying a screen, and releasing a scent.

In addition, virtual reality (VR) technologies may be combined with brain wave information to provide more realistic representations. For example, information on brain waves measured from the user, who is playing a game by using the user terminal 3, may be associated with a specific state of the user to play music or switch screens in synchronization with a specific state of the user (a specific feeling experienced by the user).

In the example described above, furthermore, a process for calibrating reference brain waves is started after the signal check function determines that no error has occurred, by way of example, but not limitation. For example, calibration may be started without executing the signal check function, or calibration may be started even when the signal check function determines that an error has occurred. For example, the signal check function may be executed after the completion of calibration. Alternatively, the signal check function may be executed alone, independent of calibration.

Further, brain waves may be affected by action potentials (bioelectric currents) produced by the movement of the user's head or the like. Thus, as a function similar to the signal check function, a function of checking the state of the user may be used. More specifically, the brain wave measurement device 2 includes, for example, a gyro sensor, and the movement of the user is checked using the gyro sensor. When non-movement of the user is confirmed, the calibration of reference brain waves and association are started. In other words, calibration and association are started when the movement of the user satisfies a predetermined movement condition.

The predetermined movement condition is a condition that limits the movement of the user, examples of which include a condition that the user's head or mouth is not moving while the user is sitting. For example, when the user's head is shaking to the left and to the right, when the user's mouth is moving, when the user is walking, or when the user is running, it is determined that the predetermined movement condition is not satisfied, and an error occurs. In this case, for example, the brain wave measurement device 2 notifies the user terminal 3 of the error, and an error message is displayed on the user terminal 3. The error message includes, for example, a message that prompts the user to make a smaller movement.

Other examples of the function similar to the signal check function include a function of checking the degree of contact between the user and the brain wave measurement device 2. More specifically, for example, the brain wave measurement device 2 includes a sensor that detects the degree of contact with the user. Examples of the degree of contact include the intensity of contact between the user and the brain wave measurement device 2, and the area of contact between the user and the brain wave measurement device 2. For example, if the degree of contact is less than a predetermined level, contact is determined to be poor and the brain wave measurement device 2 notifies the user terminal 3 of an error. Then, for example, the user terminal 3 displays a message that prompts the user to place the brain wave measurement device 2 in closer contact.

In the example described above, three specific states, namely, the normal state, the relaxed state, and the concentrated state, are used. However, the number of specific states is not limited to three. Two or less specific states or four or more specific states may be used.

In the example described above, furthermore, the brain wave measurement device 2 has been described as an example of an information processing apparatus that acquires biological information. When biological information other than brain waves is used, a device capable of detecting biological information to be measured is used.

For example, when heart rate is used as biological information, a heart rate measurement device that measures the heart rate of the user is used. The user terminal 3 associates information on the heart rate measured by the heart rate measurement device with a specific state of the user or calibrates a reference therefor. More specifically, for example, the user terminal 3 displays a guide screen to guide the user to the normal state, the relaxed state, and the concentrated state, and the heart rate of the user in each of the states is measured. A certain range of heart rates is determined for each state, for example, and is used as a reference for association. Further, for example, the user terminal 3 displays a question screen, and the reference for association is calibrated on the basis of the response to questions. The question screen includes questions for items that affect the heart rate (items estimated to affect the heart rate), such as age and gender.

A device that measures biological information is not limited to a device that is used while being in contact with the body of the user, and may be a device that is used while not being in contact with the body of the user. For example, when a voiceprint is measured as biological information, a voiceprint measurement device that measures a voiceprint without touching the user may be used. For example, when pulse waves are measured as biological information, an imaging device that is not brought into contact with the user may be used, and pulse waves may be measured from a moving image of the user captured by the imaging device.

In this exemplary embodiment, furthermore, instead of using only one piece of biological information, a plurality of pieces of biological information may be used. In other words, a plurality of pieces of biological information may be used to perform association or a plurality of pieces of biological information may be calibrated.

In the examples described above, determining reference brain waves is identified as "calibration of a reference to be used for association with a specific state". In this exemplary embodiment, for example, determining reference brain waves and determining a certain range used for association with each state may be identified as "calibration of a reference to be used for association with a specific state".

A program that implements the exemplary embodiment of the present disclosure may be provided via a communication means or may be stored in a recording medium such as a compact disc read-only memory (CD-ROM) and provided.

While an exemplary embodiment and a variety of modifications have been described, the exemplary embodiment and the modifications may be used in any combination.

It is to be understood that the present disclosure is not limited to the exemplary embodiment described above, and the present disclosure may be embodied in various forms without departing from the gist of the present disclosure.

The foregoing description of the exemplary embodiment of the present disclosure has been provided for the purposes of illustration and description. It is not intended to be exhaustive or to limit the disclosure to the precise forms disclosed. Obviously, many modifications and variations will be apparent to practitioners skilled in the art. The embodiment was chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. An information processing apparatus comprising:
a sensor configured to acquire biological information of a user, wherein the biological information is information generated by the user's body; and
a user terminal configured to:
associate the acquired biological information with a specific state of the user, and
guide the user to the specific state,
wherein a reference to be used for association with the specific state by the user terminal is calibrated by using the biological information, the biological information being acquired from the user who is guided to the specific state by the user terminal, the biological information being an average amplitude value of brain waves for a certain period of time.

2. The information processing apparatus according to claim 1, wherein the user terminal continuously guides the user to the specific state until calibration of the reference is completed.

3. The information processing apparatus according to claim 1, wherein the specific state is a plurality of specific states and the user terminal sequentially guides the user to the plurality of specific states, and
wherein the reference is a plurality of references and, for each of the plurality of specific states, a respective reference of the plurality of references to be used for association with a respective one of the plurality of specific states by the user terminal is calibrated.

4. The information processing apparatus according to claim 3, wherein the plurality of specific states include a first specific state and a second specific state, and
wherein the user terminal starts guiding the user to the second specific state after a certain period of time has elapsed after calibration of a reference to be used for association with the first specific state was completed.

5. The information processing apparatus according to claim 3, wherein the user terminal initially guides the user to a reference state for the plurality of specific states.

6. The information processing apparatus according to claim 5, wherein the reference state is a calm state of mind experienced by the user.

7. The information processing apparatus according to claim 5, wherein the user terminal associates the acquired biological information with another specific state different from the reference state among the plurality of specific states by using a difference between a reference to be used for association with the reference state and a reference to be used for association with the other specific state.

8. The information processing apparatus according to claim 3, wherein when the plurality of specific states include a specific state for which the reference is to be calibrated, re-calibration is performed only for the specific state.

9. The information processing apparatus according to claim 1, wherein the user terminal guides the user to the specific state when a movement of the user satisfies a predetermined movement condition.

10. The information processing apparatus according to claim 9, wherein the predetermined movement condition is a condition that limits the movement of the user, and
wherein when the movement of the user does not satisfy the predetermined movement condition, the user is prompted to make a smaller movement.

11. The information processing apparatus according to claim 1, wherein the user terminal guides the user to the specific state after confirmation that the user terminal correctly acquires the biological information.

12. The information processing apparatus according to claim 11, wherein when the user terminal does not confirm the biological information is correctly acquired, the user is notified that acquisition of the biological information is not confirmed.

13. The information processing apparatus according to claim 1, wherein the biological information is potential information for measuring brain waves.

14. The information processing apparatus according to claim 1, wherein the specific state is a specific feeling experienced by the user.

15. An information processing system comprising:
a sensor configured to acquire biological information of a user, wherein the biological information is information generated by the user's body; and
a user terminal configured to:
associate the acquired biological information with a specific state of the user;
guide the user to the specific state; and
calibrate a reference to be used for association with the specific state by the user terminal by using the biological information, the biological information being acquired from the user who is guided to the specific state by the user terminal, and the biological information being an average amplitude value of brain waves for a certain period of time.

16. A non-transitory computer readable medium storing a program causing a computer to execute a process for information processing, the process comprising:
acquiring biological information of a user, wherein the biological information is information generated by the user's body;
associating the acquired biological information with a specific state of the user;
guiding the user to the specific state; and
calibrating a reference to be used for association with the specific state, by using the biological information, the biological information being acquired from the user who is guided to the specific state, and the biological information being an average amplitude value of brain waves for a certain period of time.

* * * * *